United States Patent

Nielsson et al.

[11] Patent Number: 6,066,481
[45] Date of Patent: May 23, 2000

[54] CRYSTALLIZATION OF A PROTEIN WITH A SULPHUR SALT

[75] Inventors: Stig Nielsson, Lynge; Mads Aage Laustsen, Lyngby, both of Denmark

[73] Assignee: Novo Nordisk A/S, Bagsvaerd, Denmark

[21] Appl. No.: 09/141,224

[22] Filed: Aug. 27, 1998

Related U.S. Application Data

[63] Continuation of application No. PCT/DK97/00094, Mar. 3, 1997.

[30] Foreign Application Priority Data

Mar. 8, 1996 [DK] Denmark ................................. 0271/96
Sep. 17, 1996 [DK] Denmark ................................. 1003/96

[51] Int. Cl.[7] .............................. C12N 9/00; C12N 9/14; B01O 21/00
[52] U.S. Cl. ................... 435/183; 435/189; 435/195; 435/198; 435/202; 435/219; 435/220; 435/221; 435/816; 210/702
[58] Field of Search ....................... 435/183, 189, 435/198, 202, 219, 220, 221, 195, 816; 210/702

[56] References Cited

U.S. PATENT DOCUMENTS

| | | | |
|---|---|---|---|
| 1,826,467 | 10/1931 | Harteneck | 435/183 |
| 3,700,561 | 10/1972 | Ziffer | 435/183 |
| 3,795,586 | 3/1974 | Ziller et al. | |
| 5,510,461 | 4/1996 | Meuer et al. | 435/183 |

FOREIGN PATENT DOCUMENTS

| | | |
|---|---|---|
| 0 361 830 | 4/1990 | European Pat. Off. |
| WO 90/12089 | 10/1990 | WIPO |
| WO 90/13632 | 11/1990 | WIPO |
| WO 91/10678 | 7/1991 | WIPO |
| WO 93/13125 | 7/1993 | WIPO |
| WO 94/22903 | 10/1994 | WIPO |
| WO 95/01989 | 1/1995 | WIPO |

OTHER PUBLICATIONS

Lang et al. Enzyme Micorb. 14(6). pp. 479–485, 1992.
McPherson, Eur. J. Biochem, vol. 189, pp. 1–23 (1990).
Judge et al., Biotechnology and Bioengineering, vol. 48, pp. 316–323 (1995).

*Primary Examiner*—Leon B. Lankford, Jr.
*Attorney, Agent, or Firm*—Steve T. Zelson, Esq.; Reza Green, Esq.

[57] ABSTRACT

The present invention relates to a method for crystallization of a protein obtained from a protein-containing solution which involves (a) treating the protein-containing solution with a salt containing a sulphur atom having an oxidation state less than 6, and (b) recovering the protein in crystalline form.

13 Claims, 1 Drawing Sheet

CRYSTALLIZATION OF A PROTEIN WITH A SULPHUR SALT

CROSS-REFERENCE TO RELATED APPLICATIONS

This application is a continuation application of PCT/DK97/00094 filed Mar. 3, 1997 and claims priority under 35 U.S.C. 119 of Danish application nos. 0271/96 and 1003/96 filed Mar. 8, 1996 and Sep. 17, 1996, respectively, the contents of which are fully incorporated herein by reference.

TECHNICAL FIELD

The present invention relates to a simple, inexpensive and very effective method for crystallization of a protein with a salt.

BACKGROUND ART

Enzymes are usually provided as liquids or amorphous materials for industrial purposes. When not provided as liquids, they are usually provided as amorphous materials, because the known methods for crystallization of enzymes are usually regarded as too expensive to be used in an industrial scale.

There is an abundance of literature concerning crystallization of enzymes. It is difficult to generalize in respect to the outcome of specific crystallization procedures, as the art of enzyme crystallization is highly empirical.

Characteristic features of most of the hitherto known protein crystallization processes are: Pure and concentrated initial solutions, very long crystallization time, high consumption of chemicals such as salts, for reference see, e.g., *Biotechnology and Bioengineering* 48, 1995, p. 316–323.

Industrial enzyme crystallization processes using polyethylene glycol have also been described, for reference see WO 95/01989.

It has also been described that it is possible to crystallize enzymes by leaching out salts from the solution, followed by adjustment of the pH of the solution to a level around the pI of the enzyme, for reference see WO 94/22903.

SUMMARY OF THE INVENTION

In this invention it is surprisingly found that oxidizable sulphur salts are very effective as crystallization salts: They can be used in low amounts on impure solutions giving short crystallization times and high yields in a simple, inexpensive and environmentally friendly process.

Accordingly, the present invention provides a method for crystallization of a protein obtained from a protein-containing solution comprising:

(a) treatment of the protein-containing solution with a salt containing a sulphur atom having an oxidation state less than 6; and (b) recovering of the protein in crystalline form.

BRIEF DESCRIPTION OF DRAWINGS

The present invention is further illustrated by reference to the accompanying drawing, in which.

DETAILED DESCRIPTION OF THE INVENTION

Figure 1:
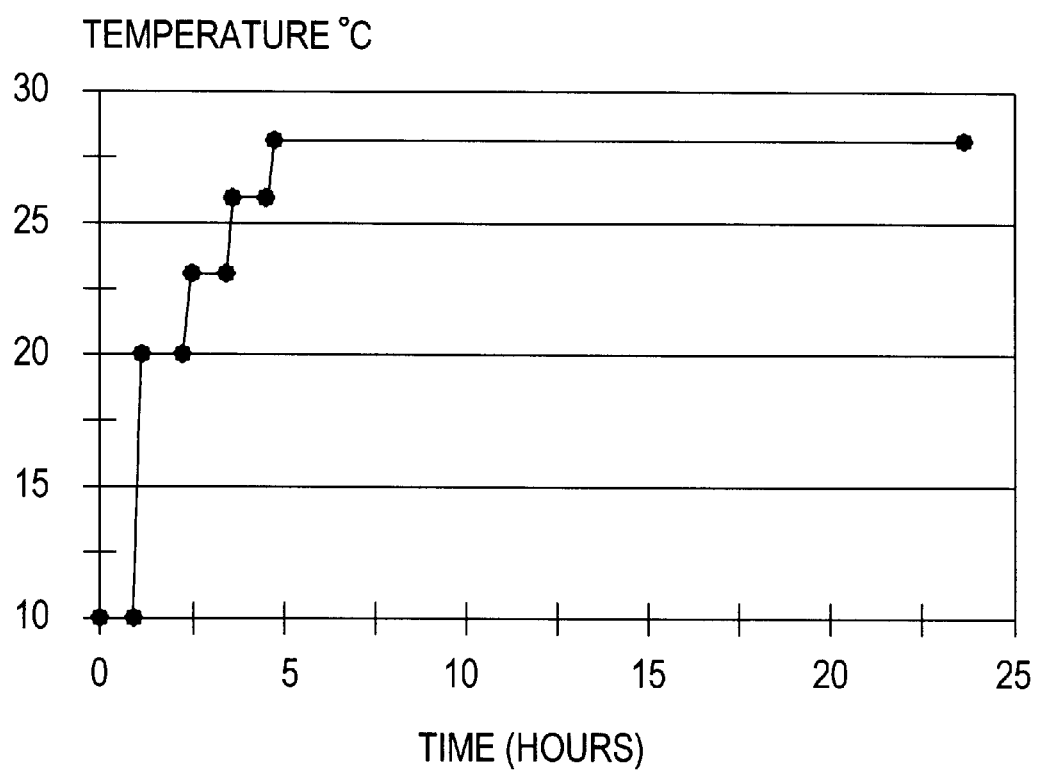
FIG. 1 shows the temperature ramp: the relation between temperature and time which is used to control the primary nucleation rate as described in Example 1.

The present invention provides a method for crystallizing a protein or a polypeptide from a protein solution, in particular from a fermentation (culture) broth.

A fermentation broth contains besides the protein of interest many other compounds such as substrate compounds, e.g., carbohydrates and salts, cells, and other metabolites such as nucleic acids and other proteins than the one of interest.

Preferably the method of the invention is applied to a fermentation broth that has first been purified by, e.g., flocculation, centrifugation, filtration, micro filtration, ultrafiltration, diafiltration, electrodialyse, adsorption, precipitation, evaporation, or any combination thereof.

As the method of the invention works very well on relatively impure solutions (see Example 1), it will normally not be necessary to purify the protein solution obtained from the fermentation broth by use of chromatographic methods before crystallization.

In a more specific embodiment, the method of invention comprises concentration of the protein containing solution by methods known per se. Such methods include concentration by ultrafiltration, by diafiltration, by dialysation, or by evaporation.

Concentration of the protein containing solution, although not essential for carrying out crystallization, is convenient from a handling and a yield perspective. For practical reasons the protein containing solution may be concentrated to a content of proteins of from 0.1 to 25% w/w, preferably of from 0.5 to 20% w/w, more preferably of from 1 to 15% w/w, even more preferably 5–12% w/w.

In a preferred embodiment, the method of the invention is applied to crystallization of an enzyme, in particular an enzyme selected from the group consisting of proteases, peptidases, lipases, amylases, cellulases, xylanases, isomerases and oxidoreductases.

Proteases

Suitable proteases to be crystallized according to the present invention include any protease which may be a fermentation product from a cell such as a microorganism. Bacterial or fungal origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the tradenames Alcalase, Savinase, Primase, Durazym, and Esperase by Novo Nordisk A/S (Denmark), those sold under the tradename Maxatase, Maxacal, Maxapem and Properase by Gist-Brocades, those sold under the tradename Purafect and Purafect OXP by Genencor International, and those sold under the tradename Opticlean and Optimase by Solvay Enzymes.

Lipases

Suitable lipases to be crystallized according to the present invention include any lipase which may be a fermentation product from a cell such as a microorganism. Bacterial or fungal origin is preferred. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a

*Pseudomonas* lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in BP 1,372,034, a *P. fluorescens* lipase, a *Bacillus lipase*, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be crystallized, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Gist-Brocades), Lipolase™ and Lipolase Ultra™ (Novo Nordisk A/S), and Lipase P "Amano" (Amano Pharmaceutical Co. Ltd.).

Amylases

Suitable amylases ($\alpha$ or $\beta$) to be crystallized according to the present invention include any amylase which may be a fermentation product from a cell such as a microorganism. Bacterial or fungal origin is preferred. Chemically or genetically modified mutants are included.

Amylases include, for example, $\alpha$-amylases obtained from Bacillus, in particular a special strain of *B. licheniformis*, described in more detail in British Patent Specification No. 1,296,839. Commercially available amylases are Duramyl™, Termamyl™, Fungamyl™ and BAN™ (available from Novo Nordisk A/S) and Rapidase™ and Maxamyl P™ (available from (Gist-Brocades).

Other useful enzymes are the CGTases (cyclodextrin glucanotransferases, EC 2.4.1.19) obtainable from e.g. Bacillus, Thermoanaerobactor or Thermoanaerobacterium.

Cellulases

In the present context, the term "cellulase" refers to an enzyme which catalyses the degradation of cellulose to glucose, cellobiose, triose and other cello-oligosaccharides.

In a preferred embodiment of the invention, the cellulase to be crystallized is an endoglucanase (EC 3.2.1.4), preferably a monocomponent (recombinant) endoglucanase.

Preferably, the cellulase is a microbial cellulase, more preferably a bacterial or fungal cellulase.

Useful examples of bacterial cellulases are cellulases derived from or producible by bacteria from the group consisting of Pseudomonas, Bacillus, Cellulomonas, Clostridium, Microspora, Thermotoga, Caldocellum and Actinomycets such as Streptomyces, Termomonospora and Acidothemus, in particular from the group consisting of *Pseudomonas cellulolyticus, Bacillus lautus, Cellulomonas fimi, Microspora bispora, Termomonospora fusca, Termomonospora cellulolyticum* and *Acidothemus cellulolyticus*.

A useful cellulase to be crystallized is an acid cellulase, which is derived from or producible by fungi from the group of genera consisting of Trichoderma, Myrothecium, Aspergillus, Phanerochaete, Neurospora, Neocallimastix and Botrytis, in particular from the group consisting of *Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum* and *Botrytis cinerea*.

Another useful cellulase to be crystallized is a neutral or alkaline cellulase, preferably a fungal neutral or alkaline cellulase, which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium, in particular from the group consisting of *Humicola insolens, Fusarium oxysporum, Myceliopthora thermophila, Penicillium janthinellum* and Cephalosporium sp., preferably from the group of species consisting of *Humicola insolens*, DSM 1800, *Fusarium oxysporum*, DSM 2672, *Myceliopthora thermophila*, CBS 117.65, and Cephalosporium sp., RYM-202.

Other examples of useful cellulases to be crystallized are variants having, as a parent cellulase, a cellulase of fungal or bacterial origin, e.g. a cellulase derivable from a strain of the fungal genus Humicola, Trichoderma or Fusarium.

Oxidoreductases

Oxidoreductases which may be crystallized according to the invention include peroxidases, and oxidases such as laccases.

Peroxidases

An enzyme exhibiting peroxidase activity may be any peroxidase enzyme comprised by the enzyme classification (EC 1.11.1.7), or any fragment derived therefrom, exhibiting peroxidase activity.

Preferably, the peroxidase employed in the method of the invention is producible by microorganisms such as fungi or bacteria. Some preferred fungi include strains belonging to the subdivision Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular *Coprinus cinereus f. microsporus* (IFO 8371), *Coprinus macrorhizus, Phanerochaete chrysosporium* (e.g. NA-12) or Trametes (previously called Polyporus), e.g. *T. versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g., *Streptomyces spheroides* (ATTC 23965), *Streptomyces thermoviolaceus* (IFO 12382) or *Streptoverticillum verticillium* ssp. verticillium.

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g., *M. virescens*.

Particularly, a recombinantly produced peroxidase is preferred, e.g., a peroxidase derived from a Coprinus sp., in particular *C. macrorhizus* or *C. cinereus* according to WO 92/16634, or a variant thereof, e.g., a variant as described in WO 93/24618 and WO 95/10602.

Laccases and Laccase Related Enzymes

In the context of this invention, laccases and laccase related enzymes contemplate any laccase enzyme comprised by the enzyme classification (EC 1.10.3.2), any chatechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The microbial laccase enzyme may be derived from bacteria or fungi (including filamentous fungi and yeasts) and suitable examples include a laccase derivable from a strain of Aspergillus, Neurospora, e.g., *N. crassa*, Podospora, Botrytis, Collybia, Fomes, Lentinus, Pleurotus, Trametes, e.g., *T. villosa* and *T. versicolor*, Rhizoctonia, e.g., *R. solani*, Coprinus, e.g. *C. plicatilis* and *C. cinereus*, Psatyrella, Myceliophthora, e.g. *M. thermophila*, Schytalidium, Polyporus, e.g., *P. pinsitus*, Phlebia, e.g., *P. radita* (WO 92/01046), or Coriolus, e.g., *C. hirsutus* (JP 2-238885), in particular laccases obtainable from Trametes, Myceliophthora, Schytalidium or Polyporus.

Salts

We have surprisingly found that low concentrations of an oxidizable sulphur salt, i.e., a salt containing at least one sulphur atom having an oxidation state less than 6, in particular a salt containing at least one sulphur atom having an oxidation state of from 2 to 4, may produce enzyme crystals from impure solutions, wherein the purity of the crystals and the yield of crystals are extraordinary good. Furthermore the morphology of the crystals may be improved compared to crystallization with other salts as the crystals are relatively large (see Example 1).

The crystallization process according to the invention passes so quickly that normally it is not necessary to add stabilizing agents or inhibitors to the protein solution.

Preferred sulphur salts according to the invention are salts of alkali or ammonium as these salts are normally easily dissolved in water, e.g.: $Na_2S_2O_3$, $Na_2SO_3$, $NaHSO_3$, $Na_2S_2O_4$, $Na_2S_2O_6 x2H_2O$, $Na_2S_3O_6$, $Na_2S_4O_6$, $Na_2S_2O_5$, $HSCH_2COONa$, $K_2S_2O_3 x1/3H_2O$, $K_2SO_3 x2H_2O$, $KHSO_2$, $K_2S_2O_6$, $K_2S_3O_6$, $K_2S_3O_6$, $K_2S_4O_6$, $K_2S_2O_4$, $Li_2SO_3 xH_2O$, $Li_2S_2O_6 x2H_2O$, $(NH_4)_2SO_3$, $LiHSO_3$, $KHSO_3$, $(NH_4)HSO_3$, $NaSCN$ or $KSCN$.

In particular a sulphite salt or a thiosulfate salt is preferred.

The sulphur salt according to the invention may be the only salt added or it may be part of a mixture which besides the sulphur salt also comprises other salts, examples of such mixtures are:

1) a mixture of a sulphur salt according to the invention and a sulphate salt;
2) a mixture of a sulphur salt according to the invention and an acetate salt;
3) a mixture of a sulphur salt according to the invention and a carbonate salt;
4) a mixture of a sulphite salt and a hydrogen sulphite salt;
5) a mixture of a sulphite salt, a hydrogen sulphite salt and an acetate salt; or
6) a mixture of a sulphite salt, a hydrogen sulphite salt and a carbonate salt.

A salt containing a halogen such as a chloride may also be included in the salt mixtures disclosed above.

In a particular embodiment of the invention the salt according to the invention is added to the protein solution at a concentration of 0.02–1.2 moles per liter, preferably at a concentration of 0.04–1.0 moles per liter, more preferably at a concentration of 0.04–0.7 moles per liter, most preferably at a concentration of 0.04–0.5 moles per liter.

The salt according to the invention may be added in one step, or it may be added in more than one step; normally the crystallization will perform satisfactorily when the salt is added in one step.

In crystallizations it may often be an advantage to reduce the agitation after the salt addition and any other adjustment to ensure against breakage of the crystals formed, this will facilitate the subsequent crystal harvest.

Adjustment of pH

The pH of the protein solution to which the salt according to the invention has been added, may be adjusted in order to find the optimum wherein the crystallization is maximized and at the same time the protein is stable. A way of finding this optimum is to run a trial, typically starting at pH 10, then perform the crystallization at pH 9, then at pH 8, then at pH 7, and so on down to pH 3, and then if it is found, e.g., that the optimum is between pH 4 and pH 5, then do a trial within this range whereby the optimum pH is found; the optimum will normally be in the range between pH 4 and pH 9.

In some cases it may also be an advantage to perform the crystallization process by ramping the pH; i.e. perform the crystallization process at various pH.

For adjustment of pH virtually any acid or base can be used. The acid may be inorganic or organic. Some examples are hydrochloric acid, sulphuric acid, sulphurous acid, nitrous acid, phosphoric acid, acetic acid, citric acid, and formic acid. Preferred acids are phosphoric acid, formic acid, citric acid, and acetic acid. Preferred bases are sodium hydroxide, potassium hydroxide, and ammonium hydroxide, in particular sodium hydroxide.

Crystallization

By using the method of the invention it may be possible to make the crystallization with a crystallization time of less than 48 hours, in particular to make the crystallization with a crystallization time of less than 36 hours, preferably to make the crystallization with a crystallization time of less than 24 hours, more preferably to make the crystallization with a crystallization time of less than 12 hours, most preferably to make the crystallization with a crystallization time of less than 6 hours, without adding any seeds to start the crystallization.

The temperature of the protein solution to be crystallized is preferably of from 5° C. to 40° C., in particular of from 10° C. to 30° C.; preferably the temperature is increased stepwise as demonstrated in Example 1, i.e., the ramp may be started at e.g. 10° C., then increased to e.g. 20° C. for 1 hour, then to e.g. 23° C. for 1 hour, then to e.g. 25° C. for 1 hour and ending at e.g. 28° C. at which temperature it may be kept for about 24 hours.

Recovery after Crystallization

The method of the invention causes the protein, in particular the enzyme, to crystallize. Recovery of the crystalline protein may be accomplished by conventional methods, e.g. by centrifugation and/or filtration and optionally drying. By using the method of the present invention the harvest properties of the crystals may be improved compared with the use of other salts such as KAc (see Example 1); because the crystals are larger this feature makes the centrifugation and/or filtration following the crystallization much easier.

If crystalline products of a very high purity are desirable, the process of the invention may be repeated, i.e. the crystalline end product of the process of the invention is redissolved and subjected to one or more additional crystallization processes.

The end product may be a crystal product or the crystals may be redissolved in order to produce e.g. a liquid protein product.

Another advantage of the present invention is that the end product contains an oxidizable sulphur salt which means that the protein, e.g. the enzyme, is stabilized against oxidations.

The invention is further illustrated in the following examples which are not intended to be in any way limiting to the scope of the invention as claimed.

EXAMPLE 1
Crystallization of a Protease using Sulphites 200 kg culture broth containing a *Bacillus lentus* protease, fermented e.g. as described in U.S. Pat. No. 3,723,250, was divided into two fractions of each 100 kg named Fraction A and Fraction B.

Each fraction was pretreated as described in Table 1 below:

TABLE 1

Pretreatment and flocculation of Broth Fraction A and Fraction B

|  | Fraction A | Fraction B |
| --- | --- | --- |
| Broth | 100 kg | 100 kg |
| Water | 200 kg | 100 kg |
| CaCl$_2$x2H$_2$O | 1 kg | 3 kg |
| NaAlO$_2$ (53–55% Al$_2$O$_3$) | 4 kg | — |
| pH | pH adjusted to pH = 5.9 | pH adjusted to pH = 7.5 |
| Cationic flocculant (20% C521) | 1 kg | 1 kg |
| Anionic flocculant (0.1% A130) | 2 kg | 1 kg |

Al-compounds significantly reduce the amount of OD$_{440\,nm}$ per activity unit, so Fraction A is more pure than Fraction B.

From each fraction the production strain was removed by centrifugation yielding two supernatants which thereafter were filtered using Seitz K900 pads. The resulting filtrates were concentrated on Asahi (6 kD) membranes. Fraction A was further diafiltered using 2 volumes of water.

In this way Concentrate B contained relatively more than Concentrate A of low molecular fermentation compounds (carbohydrates, salts, nucleic acids, other proteins, etc.). This is illustrated by measurements of the (OD$_{280\,nm}$/gram active protease) ratio, of the (OD$_{440\,nm}$/gram active enzyme) as well as (g active protease/gram Mettler drymatter) as shown in Table 2 below:

TABLE 2

Purity of Concentrate A and Concentrate B

|  | OD$_{280\,nm}$/ g active protease | OD$_{440\,nm}$/ g active protease | g active protease/ g drymatter |
| --- | --- | --- | --- |
| Concentrate A | 2081 | 233 | 0.56 |
| Concentrate B | 5411 | 821 | 0.36 |

The concentrates were subjected to various amounts of Na$_2$SO$_3$ or KAc and adjusted to pH=4.9 using a 20 w/w % phosphoric acid. A discrete temperature ramp was used to control the primary nucleation rate. The ramp started at 10° C., then increased to 20° C. for 1 hour, then to 23° C. for 1 hour, then to 25° C. for 1 hour and ended at 28° C. at which temperature it was kept for 24 hours as illustrated in FIG. 1.

The crystal suspensions were centrifuged and the crystals washed using a 5.5% CaCl$_2$ (pH=4.9) solution. The crystals were harvested using centrifugation and dissolved in 10 fold 100 % MPG and the resulting products were analyzed for OD$_{440\,nm}$ and protease activity.

The crystallization yields and purities of the final products A and B are shown in Table 3 and Table 4, respectively.

TABLE 3

Concentrate A crystallized using increasing amounts of Na$_2$SO$_3$ and KAc.

| | mMol / 1 anion Ac$^-$ or SO$_3^{2-}$ from salt | mMol / 1 anion, PO$_4^{3-}$, from phosphoric acid | Yield of active protease in final product | OD$_{440\,nm}$/ g active protease in final product | Morphology of crystals formed |
| --- | --- | --- | --- | --- | --- |
| 0% Na$_2$SO$_3$ | 0 | 0 | 0% | — | — |
| 0% KAc | 0 | 0 | 0% | — | — |
| 1% Na$_2$SO$_3$ | 79 | 105 | 39% | 29 | 15 μx 4μ rods |
| 1% KAc | 102 | 63 | <5% | — | — |
| 2% Na$_2$SO$_3$ | 158 | 180 | 82% | 16 | 5–25 μx 4μ rods |
| 2% KAc | 205 | 96 | 51% | 23 | 5–25μ needles |
| 4% Na$_2$SO$_3$ | 317 | 336 | 87% | 10 | 5–25 μx 4μ rods |
| 4% KAc | 408 | 175 | 79% | 17 | 5–25μ needles |

We find that yield and purity is increased using Na$_2$SO$_3$ instead of KAc. Additionally we find increasing thickness of the crystals produced (rods instead of needles). This is important when using filtration equipment for harvest in order to avoid penetration of the finer needles through the filter plates.

TABLE 4

Concentrate B crystallized using increasing amounts of Na$_2$SO$_3$ and KAc.

| | mMol / 1 anion Ac$^-$ or SO$_3^{2-}$ from salt | mMol / 1 anion, PO$_4^{3-}$, from phosphoric acid | Yield of active protease | OD$_{440\,nm}$/ g active protease in final product | Morphology |
| --- | --- | --- | --- | --- | --- |
| 0% Na$_2$SO$_3$ | 0 | 0 | 0% | — | — |
| 0% KAc | 0 | 0 | 0% | — | — |
| 4% Na$_2$SO$_3$ | 317 | 230 | 73% | 53 | 30 μx 4μ rods |
| 4% KAc | 408 | 202 | <5% | — | — |
| 5% Na$_2$SO$_3$ | 396 | 279 | 81% | 51 | 30 μx 4μ rods |
| 5% KAc | 510 | 242 | <5% | — | — |
| 6% KAc | 612 | 285 | <5% | — | — |
| 8% KAc | 816 | 387 | <5% | — | — |
| 10% KAc | 1020 | 434 | 49% | 102 | 25μ needles |

On this much more impure concentrate we find that yield and purity is indeed increased using Na$_2$SO$_3$ instead of KAc.

We need as high as 10% KAc in order to crystallize but only 4% of $Na_2SO_3$. Also we find increased thickness of the crystals.

The cost difference using KAc or $Na_2SO_3$ is neglectable regarding the price per Kg of raw material, however, since less salt is needed in the case of $Na_2SO_3$ than in the case of KAc this favours $Na_2SO_3$.

EXAMPLE 2
Crystallization of an Amylase using Thiosulphate

100 Kg culture broth containing a *Bacillus licheniformis* amylase, fermented e.g. as described in GB 1,296,839, was subjected to the following treatment:

TABLE 5

Pretreatment of *Bacillus licheniformis* broth

|  | Fraction |
| --- | --- |
| Broth | 100 Kg |
| Water | 100 Kg |
| $CaCl_2 \times 2H_2O$ | 5 Kg |
| $Na_3PO_4$ | 1 Kg |
| $NaAl_2O_3$ | 2 Kg |
| pH adjusted using 20% Formic acid | pH = 8.0 |
| Cationic flocculant (20% C521) | 2 Kg |
| Anionic flocculant (0.1% A130) | 3 Kg |

The production strain was removed by drum filtration yielding a filtrate which successively was germfiltered using Seitz EK1 filter pads. The resulting filtrate was concentrated using evaporation to a drymatter contents of 15% (measured as refractive index). The purity of the resulting concentrate is illustrated by the ratio of ($OD_{440\ nm}$/g active amylase) and the ratio of active enzyme/drymatter (g enz/g drymatter).

TABLE 6

Purity of Concentrate before crystallization starts.

|  | $OD_{440\ nm}$/g active amylase | g enz/ g drymatter |
| --- | --- | --- |
| Concentrate | 70 | 0.54 |

The concentrate was further subjected to various amounts of potassium acetate, sodium thiosulphate and sodium sulphate and adjusted to pH=7.3 using a 13 w/w % NaOH solution and left for 24 hours of crystallization time at 28° C.

The crystal suspensions were harvested by centrifugation. The crystal cakes were dissolved and formulated in 10 fold by weight of a 50% MPG solution. The resulting formulated products were analyzed for $OD_{440\ nm}$ and amylase activity.

Amylase activity analysis is based on the digestion of a p-nitrophenyl-alfa, D-maltoheptaoside (pNP-$G_7$) by the α-amylase. The substrate, pNP-$G_7$, is degraded by the amylase to pNP-$G_3$ and pNP-$G_4$. pNP-$G_3$ is further degraded by an excess amount of α-glucosidase to glucose and the yellow p-nitrophenol. The reaction is followed in situ whereby the change in absorbance per time unit can be calculated. This figure is a measure of the reaction rate and the enzyme activity. In order to avoid interference from the protease, PMSF (Phenyl Methyl Sulfonyl Floride) is added to the test solution.

The yields and purities of the final products are shown in Table 7.

TABLE 7

Concentrate subjected to increasing amounts of three different salts and crystallized at pH = 7.3 and 28° C. showing yield and purity.

| Amount of salt | Yield of active amylase in formulated product | | | $OD_{440\ nm}$/ g active amylase in formulated product | | |
| --- | --- | --- | --- | --- | --- | --- |
| (w/w %) | KAc | $Na_2SO_4$ | $Na_2S_2O_3$ | Kac | $Na_2SO_4$ | $Na_2S_2O_3$ |
| 0.25% | 0% | 0% | 24% | — | — | 31 |
| 0.5% | 0% | 0% | 72% | — | — | 26 |
| 1% | 0% | 11% | 80% | — | 39 | 25 |
| 3% | 44% | 72% | — | 30 | 26 | — |

We find, surprisingly, that yield is increased using sodium thiosulphate ($Na_2S_2O_3$) as crystallization agent. In other words, we can increase yield substantially and even gain improved purity using thiosulphate.

The cost difference using either KAc or $Na_2S_2O_3$ is neglectable regarding the price per Kg of raw material, however since less salt is used in the case of $Na_2S_2O_3$ than in the case of KAc this favours $Na_2S_2O_3$ for crystallization of this amylase.

EXAMPLE 3
Crystallization of a Protease using Sodium Thiosulphate

100 Kg culture broth containing a *Bacillus lentus* protease, fermented e.g. as described in U.S. Pat. No. 3,723,250, was subjected to the following treatment:

|  | Amount |
| --- | --- |
| Broth | 100 Kg |
| Water | 200 Kg |
| $CaCl_2 \times 2H_2O$ | 1 Kg |
| $NaAlO_2$ (53–55% $Al_2O_3$) | 1 Kg |
| pH | 5.9 |
| Cationic flocculant (20% C521) | 1 Kg |
| Anionic flocculant (0.1% A130) | 5 Kg |

The production strain was removed by drum filtration yielding a filtrate which was further filtered using Seitz K900 filter plates and subsequently germfiltered using Seitz EK1 filter pads. The resulting filtrate was concentrated on Asahi (6 kD) membranes.

The purity of the resulting concentrate is illustrated by the ratio of ($OD_{440\ nm}$/g active protease) and the ratio of ($OD_{280\ nm}$/g active protease) in Table 8 below.

TABLE 8

Purity of Concentrate before crystallization starts.

|  | $OD_{440\ nm}$/g active protease | $OD_{280\ nm}$/g active protease |
| --- | --- | --- |
| Concentrate | 179 | 2498 |

The concentrate was further subjected to various amounts of potassium acetate and sodium thiosulphate and adjusted to pH=4.9 using a 20 w/w% HCOOH solution and left for 24 hours of crystallization time at 28° C.

The crystal suspensions were harvested by centrifugation. The crystal cakes were washed using 1 fold by weight of a 5.5% $CaCl_2$ solution. The resulting crystal cakes were dissolved and formulated in 10 fold by weight of a 70% MPG solution.

The resulting formulated products were analyzed for protease activity. Protease activity was measured using a Kinetic Dimethyl Casein assay.

The yields of the final products are shown in

TABLE 9

| Amount of salt | Yield of active protease in formulated product | | Morphology | |
|---|---|---|---|---|
| (w/w %) | KAc | $Na_2S_2O_3$ | Kac | $Na_2S_2O_3$ |
| 1% | 0% | 81% | — | Needles |
| 2% | 13% | 93% | Few Rods 10–25 mm | Rods 5–30 mm |
| 4% | 94% | 98% | Rods 10–25 mm tendency to amorphous | Rods 5–30 mm |
| 7% | 99% | 99% | Amorphous | Rods 5–30 mm |

Table 9. Yield and morphology of concentrate subjected to increasing amounts of two different salts and crystallized at pH=4.9 at 28° C.

We find surprisingly that yield is increased significantly by using sodium thiosulphate ($Na_2S_2O_3$) as crystallization agent at low salt concentrations. Furthermore we gain improved crystal morphology as can be seen from Table 9.

What is claimed is:

1. A method for crystallization of a protein from a protein-containing solution, said method comprising:
   (a) treating the protein-containing solution with a crystallization-effective amount of a salt containing a sulfur atom having an oxidation state less than 6, wherein the concentration of said sulfur-containing salt in said solution is between about 0.04–0.7 M; and
   (b) recovering the protein in crystalline form.

2. The method according to claim 1, wherein the sulfur atom has an oxidation state of from 2 to 4.

3. The method according to claim 1, wherein the salt is a sulfite salt or a thiosulfate salt.

4. The method according to claim 1, wherein the salt is selected from the group consisting of $Na_2S_2O_3$, $Na_2SO_3$, $NaHSO_3$, $Na_2S_2O_4$, $Na_2S_2O_6 \cdot 2H_2O$, $Na_2S_3O_6$, $Na_2S_4O_6$, $Na_2S_2O_5$, $HSCH_2COONa$, $K_2S_2O_3 \cdot 1/3H_2O$, $K_2SO_3 \cdot 2H_2O$, $KHSO_2$, $K_2S_2O_6$, $K_2S_3O_6$, $K_2S_4O_6$, $K_2S_2O_4$, $Li_2SO_3 \cdot xH_2O$, $Li_2S_2O_6 \cdot 2H_2O$, $(NH_4)_2SO_3$, $LiHSO_3$, $KHSO_3$ and $(NH_4)HSO_3$.

5. The method according to claim 1, wherein the protein-containing solution comprises more than one protein.

6. The method according to claim 1, wherein the protein-containing solution is obtained from a fermentation broth.

7. The method according to claim 6, wherein the fermentation broth prior to the salt treatment is purified by centrifugation, filtration, microfiltration, ultrafiltration, diafiltration, electrodialyse, precipitation, evaporation, or a combination thereof.

8. The method according to claim 6, wherein one or more flocculating agents are added to the fermentation broth prior to the salt treatment.

9. The method according to claim 1, wherein the sulfur-containing salt is added to the protein solution at a concentration 0.04–0.5 moles per liter protein solution.

10. The method according to claim 1, wherein the protein solution is concentrated to a content of proteins of from 0.1 to 25% w/w.

11. The method according to claim 1, wherein the protein is an enzyme.

12. The method according to claim 11, wherein the enzyme is a protease, a lipase, a cellulase, an amulase or an oxidoreductase.

13. The method according to claim 1, wherein the pH of the protein-containing solution is between 4 and 9.

* * * * *